United States Patent [19]

Evans et al.

[11] Patent Number: 4,502,490

[45] Date of Patent: Mar. 5, 1985

[54] PATIENT MONITORING EQUIPMENT, PROBE FOR USE THEREWITH, AND METHOD OF MEASURING ANESTHESIA BASED ON OESOPHAGAL CONTRACTIONS

[75] Inventors: John M. Evans, Abingdon; Colin C. Wise, Penarth, both of England

[73] Assignee: Antec Systems Limited, England

[21] Appl. No.: 314,413

[22] Filed: Oct. 23, 1981

[30] Foreign Application Priority Data

Oct. 28, 1980 [GB] United Kingdom ............... 8034669
Dec. 11, 1980 [GB] United Kingdom ............... 8039741

[51] Int. Cl.³ .............................................. D61B 5/10
[52] U.S. Cl. ..................................................... 128/780
[58] Field of Search ............... 128/721, 733, 739, 741, 128/747, 748, 774, 780, 782, 630

[56] References Cited

U.S. PATENT DOCUMENTS

| | | | |
|---|---|---|---|
| 3,171,892 | 3/1965 | Pantle | 128/698 |
| 3,898,983 | 8/1975 | Elam | 128/782 |
| 4,214,593 | 7/1980 | Imbruce et al. | 128/780 |
| 4,231,255 | 11/1980 | Haski et al. | 128/774 |
| 4,235,242 | 11/1980 | Howson et al. | 128/695 |

FOREIGN PATENT DOCUMENTS 790091 9/1935 France .......................... 128/780

OTHER PUBLICATIONS

Ask et al., "Medical & Biological Engineering and Computing" vol. 19, No. 4, Jul. 1981, pp. 501-503.

*Primary Examiner*—William E. Kamm
*Attorney, Agent, or Firm*—Cushman, Darby & Cushman

[57] ABSTRACT

A method of monitoring the depth of anaesthesia of a patient, comprising stimulating contractions in the oesophagus of the patient, for example using an inflatable oesophageal balloon, obtaining signals indicative of the oesophageal contractions using a sensor, and deriving from the signals an output indicative of the rate of occurrence of signals having a magnitude greater than a preset threshold value, and apparatus for carrying out the method.

An alternative aspect comprises assigning a score value to each of a plurality of different bodily functions of a patient, for example heart rate, blood pressure, degree of sweating, and formation of tears, the said score values being indicative of a depth of anaesthesia or sedation, summing the score values, and producing an output from the summed score values indicative of the amount of anaesthetic to be fed to the patient.

49 Claims, 11 Drawing Figures

PATIENT MONITORING EQUIPMENT, PROBE FOR USE THEREWITH, AND METHOD OF MEASURING ANESTHESIA BASED ON OESOPHAGAL CONTRACTIONS

BACKGROUND AND SUMMARY OF THE PRESENT INVENTION

This invention relates to patient monitoring equipment, probe for use therewith, and method of measuring anesthesia based on oesophagal contractions. It has application in monitoring the depth of anaesthesia of patients to whom anaesthetic or sedative drugs are administered. The term anaesthesia is used herein in its broadest sense and is intended to include not only anaesthesia for surgery, but also the lighter levels of anaesthesia or sedation used in critically ill patients receiving intensive care. The term anaesthetic is to be understood accordingly.

The response of individual patients to drugs is highly variable. Especially in the case of anaesthetic drugs an anaesthetist is required to employ a considerable degree of clinical judgement in order to obtain an optimum effect. Clinical anaesthesia is not an "on-off" state but a state of unconsciousness and variable reflex suppression produced by one or more drugs. It is traditional to describe the degree of reflex suppression as the depth of anaesthesia. At present the depth of anaesthesia is judged by the change in various clinical signs produced in response to surgical stimulus. It would be of great assistance if some objective information were available indicating the depth of anaesthesia. Attempts have been made to use indirect measurements of a patient's vital physiological functions such as heart rate, blood pressure and electroencephalogram (EEG) waveforms to indicate depth of anaesthesia. No one of these measurements alone has proved to be a sufficiently reliable index of anaesthesia.

An article by P. Suppan in the British Journal of Anaesthesia, (1972) 44, p. 1263 describes the use of pulse rate as an indicator of depth of anaesthesia, and describes furthermore the use of a feed-back system to automatically control anaesthetic administration. The article also describes the possibility of using blood pressure as an indicator of the depth of anaesthesia, but there is no suggestion of the combined use of the parameters, or any suggestion that combining two or more measurements to produce a "score" can provide a more reliable indication of depth of anaesthesia.

M. Dubuis, D. E. Scott, and T. M. Savege, in an article in Annals Anaesthesia, France (1979) 3, p 215 describe the use of EEG as an indicator of the after effects of anaesthesia.

Electronically processed EEG signals have been employed to monitor the level of electrical activity in the brain during anaesthesia. A review of this and other applications of EEG monitoring is given in Monitoring Cerebral Function (author P. F. Prior, published by Elsevoir (North-Holland Biomedical Press, 1979, Amsterdam).

Finally J. S. Stewart in The Lancet (1969) 1, p 1305 describes a monitoring system for drawing the attention of a clinician to a deteriorating condition of a patient, using a combination of various parameters, such as heart rate, blood pressure, and oxygen tension. There is, however, no suggestion in the Stewart article of the use of a similar system to measure depth of anaesthesia.

We have discovered that the muscular activity in the oesophagus is related to the depth of anaesthesia. During light anaesthesia there is a great deal of smooth muscle activity in the form of periodic contractions. During deep anaesthesia there is little oesophageal smooth muscle activity. We have consistently observed this relationship between oesophageal activity and depth of anaesthesia with most common anaesthetic agents. Changes in oesophageal muscle activity cause corresponding changes in intra-lumenal oesophageal pressure. Thus, by insertion of a balloon-type catheter, or some other suitable pressure probe, into the oesophagus, and measuring the internal pressure in the oesophagus, it is possible to obtain an indication of the depth of anaesthesia.

The pressure changes produced by oesophageal contraction generally last 2-4 seconds and occur at frequencies of up to 4 or 5 per minute during light anaesthesia. Occasionally there are short periods of rapid contractions at rates of up to 15 per minute accompanied by high resting pressures between contractions.

Oesophageal activity has in the past been observed for a variety of purposes, for example N. E. Leatherman in an article in Critical Care Medicine (1978) Vol 6, No 3 p189 describes the use of an oesophageal balloon for measuring intra-pleural pressure in the monitoring of acutely ill patients. However, we are not aware of any proposals for using measurements of oesophageal activity to monitor depth of anaesthesia.

We have also discovered that, whether or not oesophageal contractions are used as a measure of the degree of anaesthesia, increased reliability in the quantification by the anaesthetist of depth of anaesthesia can be obtained if a plurality of different bodily functions are observed, and a score value assigned to each in accordance with certain parameters. The score values may then be summed to produce a total score indicative of the degree of anaesthesia of the patient.

In one aspect of the method of monitoring anaesthesia proposed herein, signals are produced indicative of the contractions in the oesophagus of a patient, and an output is derived from the signal indicative of the degree of anaesthesia of the patient.

According to a first aspect of the invention, there is provided patient monitoring apparatus, comprising a sensor for providing signals indicative of contractions in the oesophagus of a patient, and means for deriving from the said signals an output indicative of the depth of anaesthesia of the patient.

Preferably the output is derived from the rate of generation of signals produced by oesophageal contraction. Accordingly, in one embodiment of this aspect of the invention, there is provided patient monitoring apparatus comprising a sensor for producing signals indicative of contractions in the oesophagus of a patient, and means for producing an output indicative of the rate of occurrence of such contractions. Alternatively, an output may be derived from the amplitude of such signals.

The changes in pressure that occur and which are picked up by the sensor will be not only pressure changes due to oesophageal contraction but also pressure changes resulting from movement of the heart adjacent to the oesophagus and changes in intrathoracic pressure due to ventilation of the lungs. The pressure changes produced by ventilation and movement of the heart are relatively small and are usually less than 20 mm Hg, typically about 10 mm Hg, when measured with a balloon-type catheter of the type hereinafter described. In contrast oesophageal contractions produce changes in intra-lumenal pressure which may be as high as 100 mm Hg and are usually in excess of 20 mm Hg. In order therefore to eliminate signals arising out of activity not due to oesophageal contractions it is desirable to set a threshold value of pressure below which no signals are utilised for monitoring purposes. This can be done by providing the apparatus with discriminating means for rejecting signals of less than a desired threshold magnitude. The threshold magnitude is preferably substantially greater than, for example twice as great as the magnitude of signals produced by forced ventilation of the lungs of the patient.

In a further embodiment of this aspect of the invention, there is therefore provided patient monitoring apparatus, comprising a sensor for producing signals indicative of contractions in the oesophagus of a patient, and discriminating means for accepting only signals of greater than a predetermined magnitude.

Furthermore in order to minimise spurious signals arising from irregularities in the pressure waveform, an inhibition period may be provided immediately following each contraction in excess of the threshold. In the inhibition period no contractions are recognised. A convenient value for threshold pressure is 20-25 mm Hg and for the inhibition period a time of from 5 to 10 seconds may be suitable.

The rate of generation of contraction signals can be derived from a measurement of the time intervals between successive contractions. The contractions may not occur at regular intervals and a rate derived directly in this way would fluctuate frequently. A measurement of such time interval could be stored and averaged to overcome this instability. A more stable and representative rate is obtained by providing means for counting the number of oesophageal contractions over a period of time and indicating the mean or average rate.

In carrying out the invention therefore it is convenient to make the period of time over which the contractions are averaged a moving and adjustable time "window". A convenient value for such a time "window" is up to nine minutes, preferably from 3 to 9 minutes.

It is possible to provoke oesophageal contractions. These provoked contractions are similar to spontaneous contractions but can be provoked at a depth of anaesthesia sufficient to suppress spontaneous contractions. As anaesthesia is deepened the oesophageal response to provocation diminishes. Thus the provision of means for provoking oesophageal contractions allows deeper levels of anaethesia to be monitored.

According to yet a further embodiment of this aspect of the invention, there is therefore provided patient monitoring apparatus, comprising means for stimulating contractions in the oesophagus of a patient and a sensor for producing signals indicative of contractions in the oesophagus of the patient.

The amplitude of the provoked oesophageal response is, in part, related to the depth of anaesthesia. Thus in addition to the rate of oesophageal contractions, the amplitude of the provoked response may be used as a guide to the depth of anaesthesia. Oesophageal contractions may be provoked by the application of a mechanical or electrical stimulus to the oesophagus or contiguous structures for example the pharynx, larynx or trachea. A convenient means of provoking oesophageal contractions is an air or liquid filled inflatable balloon inserted into the trachea or more preferably, the oesophagus.

Since the equipment described above provides an indication of the depth of anaesthesia it is possible to use the indication obtained to control a drug delivery system to achieve a desired depth of anaesthesia.

According to the invention in another aspect anaesthetic control equipment comprises a sensor for providing signals indicative of contractions in the oesophagus of a patient, for example a probe adapted to be inserted into the oesophagus of the patient and means for controlling the delivery of anaesthetic drugs to the patient in accordance with a parameter of the signals so obtained to achieve a desired depth of anaesthesia.

A suitable parameter is the rate of generation of such signals, preferably averaged over a period of time. However, an amplitude measurement of such signals may be used, particularly where provoked contractions are being measured.

It will be appreciated that the anaesthetic control equipment set out above operates as an automatic closed-loop control system.

As mentioned above we have also discovered that, whether or not oesophageal contractions are used as a measure of the degree of anaesthesia, increased reliability in the quantification by the anaesthetist of depth of anaesthesia can be obtained if a plurality of different bodily functions are observed, and a score value assigned to each in accordance with certain parameters, the score values then being be summed to produce a total score indicative of the degree of anaesthesia of the patient.

According to a further aspect of the invention, there is provided a method of monitoring the degree of anaesthesia or sedation of a patient, which method comprises assigning a score value to each of a plurality of different bodily functions, the said score values being indicative of a depth of anaesthesia or sedation, and summing the score values to obtain a total score indicative of the degree of anaesthesia or sedation of the patient.

The invention also provides patient monitoring apparatus, which comprises means for assigning a score value to each of a plurality of different bodily functions of a patient, the said score values being indicative of a depth of anaesthesia or sedation, means for summing the score values, and means for producing an output from the summed score values indicative of the amount of anaesthetic to be given to the patient.

In carrying out the invention means may be provided for measuring one or more of the said bodily functions and for automatically generating a score value from the measured value. This is particularly suitable for functions such as heart rate and blood pressure. Alternatively the means for assigning a score value to a bodily function may take the form of a keypad, for entering a score value in accordance with a clinical assessment of a selected bodily function. The apparatus of the invention preferably includes means for displaying the resultant score.

Examples of bodily functions that may be measured are EEG activity, cardiac output and oxygen consumption. Specific cardiac function indices that may be measured include blood pressure (normally systolic blood pressure, although diastolic or mean blood pressure may alternatively be used) and heart beat rate. Functions in which clinical assessments may be made and a score value assigned via the keypad are the degree of sweating and the formation of tears. Values of bodily functions which are readily measured by instruments, such as systolic blood pressure and heart beat rate may of course be measured by conventional methods, and score values assigned using the keypad.

Alternatively, or additionally to the above-listed functions, other bodily functions may be measured or assessed.

We have found that because the summed score value relates to a plurality of different bodily functions the score is a much more reliable indication of the depth of anaesthesia than measurement of any one individual function by itself.

Means may be included for recording the total score and if desired the individual score values. It may be convenient to record other associated information, for example the time at which the measurements are taken.

The displayed score can be compared with a desired score in a comparator to derive a score error and the rate of administration of appropriate drugs may then be determined in accordance with the score error to achieve a desired depth of anaesthesia. By providing means for entering an initial rate of administration into the equipment and then modifying this rate by the score error a required rate of administration of a drug may be obtained, displayed and automatically controlled.

As indicated above the score obtained may be used to automatically control the delivery of drugs to a patient.

It is desirable to provide a clock which provides control signals to the measuring means to update the score values at regular intervals and where one or more score value assessments are included it may be desirable to include means for prompting the clinician or anaesthetist to enter his current assessments.

BRIEF DESCRIPTION OF THE ACCOMPANYING DRAWINGS

A number of particularly preferred embodiments of the invention wil now be described with reference to the accompanying drawings in which.

Figure 1:
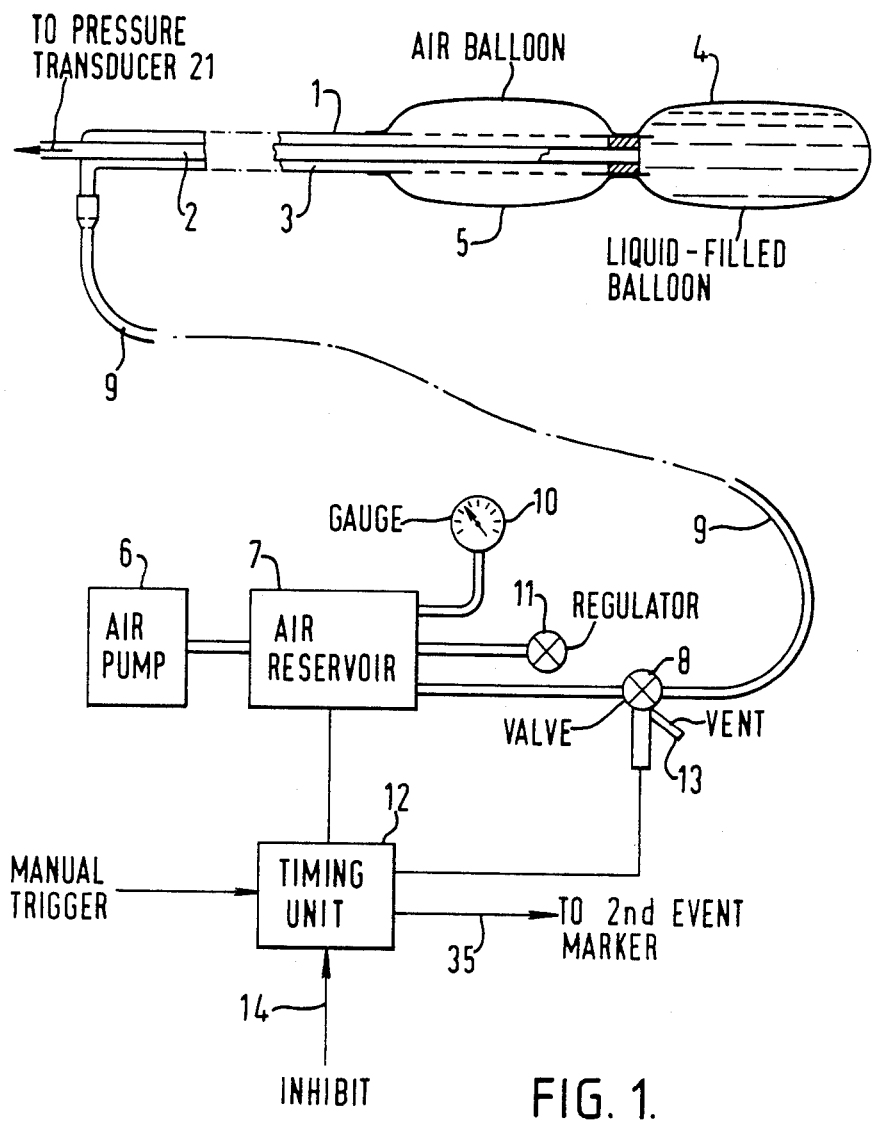
FIG. 1 illustrates a probe adapted to be inserted into the oesophagus together with associated equipment.
Figure 2:
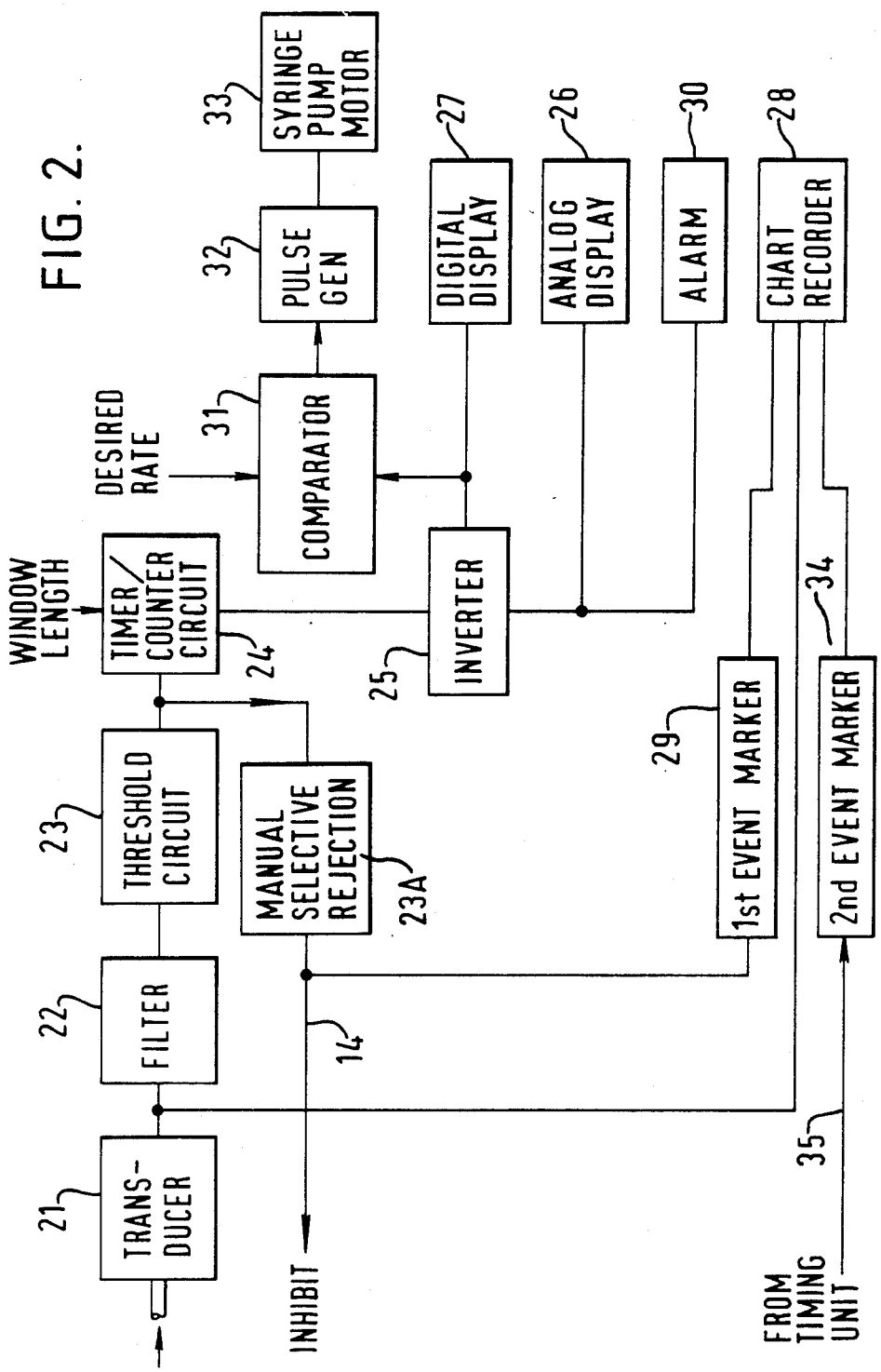
FIG. 2 illustrates monitoring and control equipment suitable for use with the probe of FIG. 1.
Figure 6:
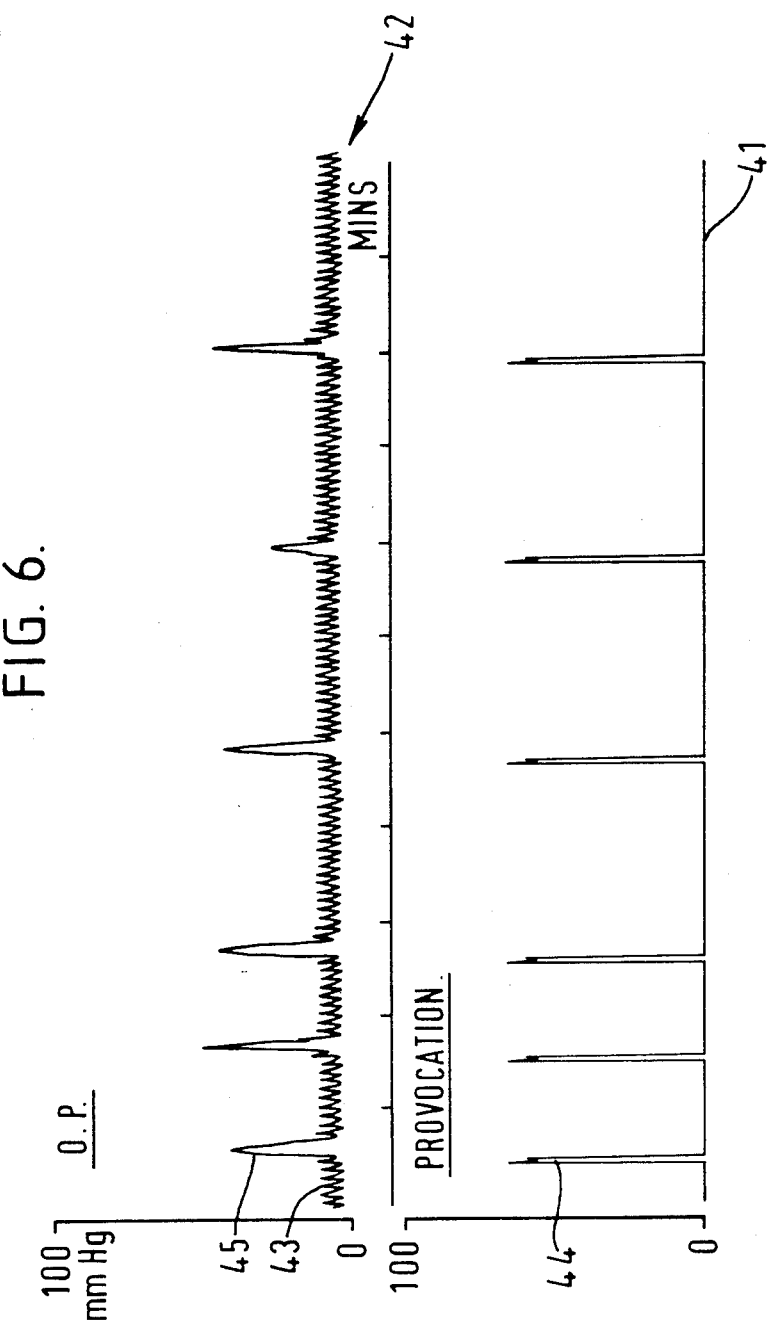
Figure 7:
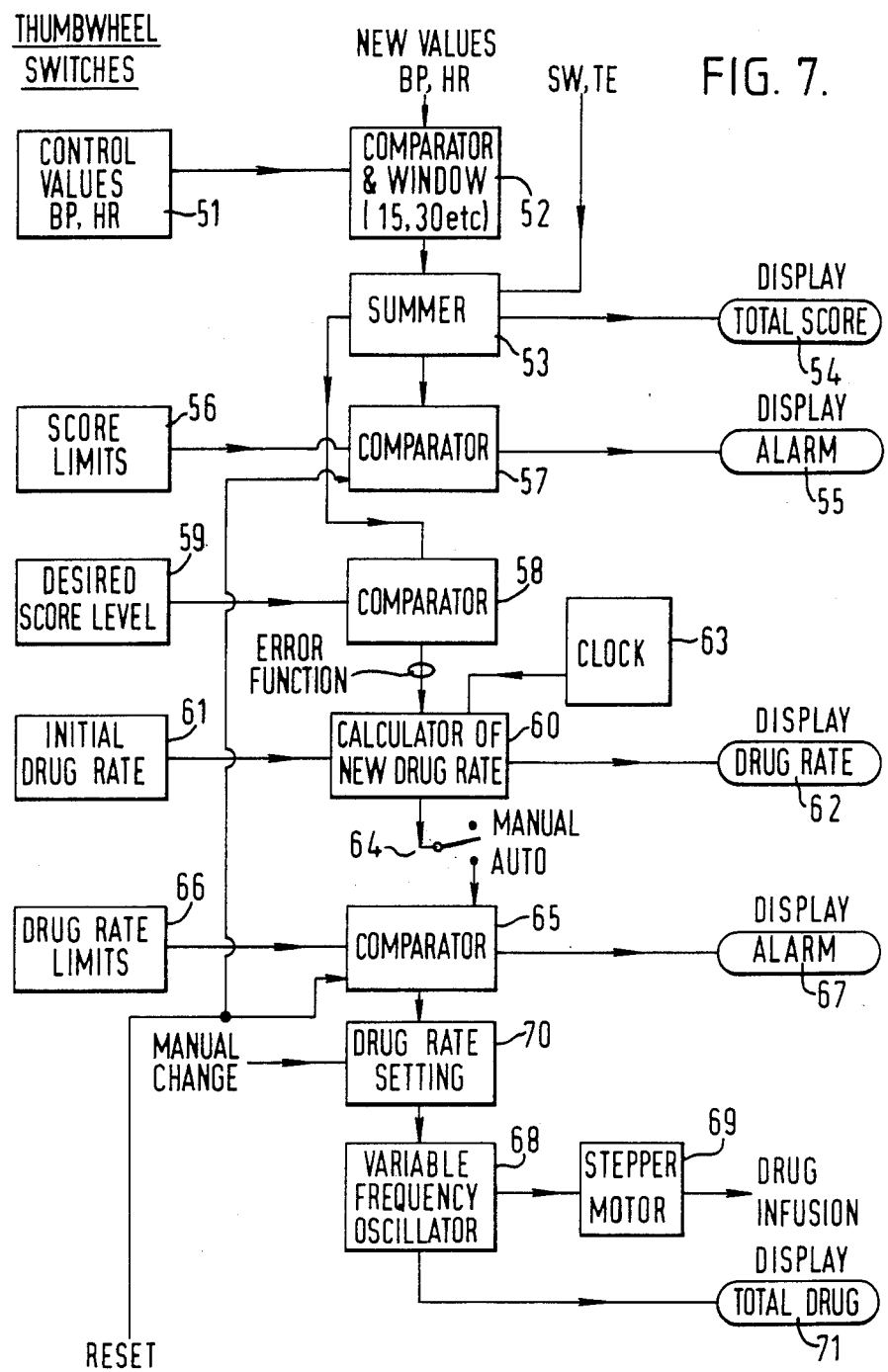
Figure 8:
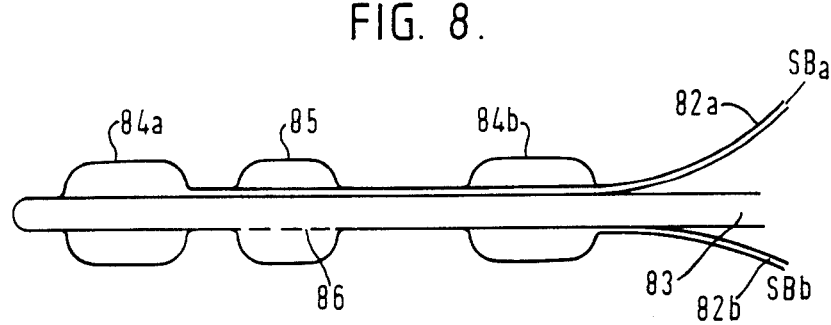
Figure 9:
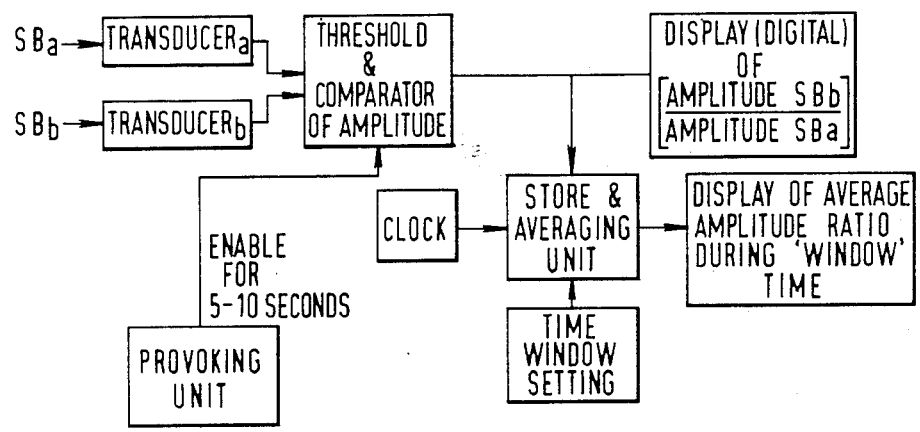

FIG. 6 shows a typical trace obtained with apparatus as illustrated in FIGS. 1 and 2 showing provoked oesophageal contractions, FIG. 7 is a block diagram of apparatus in accordance with the second aspect of the invention, FIG. 8 illustrates yet a further alternative construction of an oesophageal probe, and FIG. 9 is a block schematic diagram of an electronic circuit suitable for use with the probe of FIG. 8.

DETAILED DESCRIPTION OF THE PREFERRED EXEMPLARY EMBODIMENTS

Referring now to FIG. 1 there is shown therein a probe which is adapted to be inserted into an oesophagus. The probe comprises a hollow flexible stem 1 which contains two passageways 2 and 3. At the end of the probe there is provided a balloon 4 which is connected to passageway 2 and adjacent to balloon 4 is a further balloon 5 coupled to passageway 3. Balloon 4 is liquid-filled and passageway 2 is coupled to a pressure transducer so that the external pressure applied to balloon 4 can be monitored. Balloon 5 is connected to passageway 3. A suitable length for stem 1 is about 100 cm while the total length of the two balloons 4 and 5 can be about 10 cms. The two balloons each have a maximum diameter of approximately 2 cms.

Passageway 3 is connected to an air supply line 9. An air-pump 6 supplies a reservoir 7 which feeds supply line 9 through a valve 8. A pressure gauge 10 is coupled to reservoir 7. In an alternative and preferred embodiment, gauge 10 is coupled to line 9 so as to measure directly the provoking pressure. Reservoir 7 also has a regulating valve 11 which can be adjusted to prevent excessive rise in the pressure in reservoir 7. Valve 8 is controlled by a timing unit 12.

In use of the equipment shown in FIG. 1 probe 1 is inserted into the oesophagus so that the balloon 4 is in the lower part of the oesophagus, in an adult, typically 35 cm from the incisor teeth, and the timing unit 12 functions to control valve 8 to connect reservoir 7 to intermittently inflate balloon 5. At the end of each inflation period valve 8 connects line 9 to a vent 13 to allow balloon 5 to deflate. With reservoir 7 having a volume of approximately 200 cc and being held at a pressure of around 200 mm Hg and with balloon 5 having an inflated volume of about 5 cc the opening of valve 8 will cause full and rapid expansion of balloon 5 to its maximum capacity. It is convenient to hold balloon 5 inflated for periods of 5 seconds or there-abouts with the intervals between inflations being in the range of 1–10 mins.

In order to safeguard against deleterious effects on a patient arising out of rupture of balloon 5 it may be desirable to provide means for limiting the volume or rate of airflow out of reservoir 7. A second valve may be provided, operated by the timing unit 12, between the air pump 6 and the reservoir 7 and open when valve 8 is closed, to restore pressure in the reservoir 7 only when the reservoir is not directly connected to balloon 5.

Any contraction of the oesophagus which is either spontaneous or else is triggered by inflation of balloon 5 is monitored by liquid-filled balloon 4 and the pressure signal therefrom fed through passageway 2 to a pressure transducer (not shown).

The monitor balloon 4 described above is liquid filled, preferably with water. It is however possible to use an air or gas filled balloon for monitoring purposes although in such cases there may be a loss of fidelity in the recording of pressure amplitude. Alternatively in place of a balloon a catheter tip transducer can be inserted into the oesophagus in a soft balloon sleeve, in the position of balloon 4.

While a separate monitoring balloon 4 and provoking balloon 5 have been described with reference to FIG. 1 it is possible to replace the two balloons by a single balloon which fulfils both functions. In such a case a switching valve is required which normally connects the balloon to the pressure transducer but which is switched to valve 8 whenever a provoking stimulus is called for by the timing unit 12.

Timing unit 12 is optionally provided with an inhibit input along a line 14. When an inhibit pulse is received timing unit 12 does not function for a set period thereafter so that inflation of provoking balloon 5 is inhibited during that period. The inhibit pulses are derived from the pressure transducer 21 to which balloon 4 is coupled as shown in FIG. 2. Use of the inhibit pulses ensures that when there are spontaneous contractions operation of the provoking balloon, which is unnecessary, is prevented. A further option provides for manual triggering of timing unit 12 to operate valve 8.

FIG. 2 shows monitoring and control equipment in block diagrammatic form. The pressure signal obtained from the balloon 4 shown in FIG. 1 is fed to a transducer 21 which provides an output signal of magnitude proportional to the amplitude of the pressure signal fed to it. Transducer 21 may include offset and gain controls.

The output signal from transducer 21 includes not only major signals derived from oesophageal contractions but also other signals which arise from heartbeats and lung ventilation as well as other background signals including noise. The output from transducer 21 is applied to a filter 22 to remove low level background signals and thence to an adjustable threshold circuit 23 to block all remaining signals below a set level. Since the oesophageal contractions result in pressure signals of much higher level of amplitude than signals from other sources the setting of an appropriate threshold level in circuit 23 ensures that the output therefrom comprises signals due to the oesophageal contractions only.

The signals from circuit 23 are utilised to provide a count of events in a moving time "window". The count is made in a timer/counter circuit 24 into which the desired lengths or duration of the time "window" is entered. Conveniently circuit 24 has a plurality of registers each of which records the inputs received from circuit 23 in a fixed time period (e.g. one minute) in succession. The number of the most recently filled registers that contribute their contents to the summation is determined by the length of the time "window". Thus for one minute registers and a time "window" of four minutes the four last-filled registers are summed and their sum is outputted. The above example of a one minute time period and a time window of four minutes is purely to illustrate the manner of operation of circuit 24 and a different time period can be provided in the circuit and the length of the time "window" may be adjustable for greater or smaller durations than the figure quoted. The summation of the register contents may be adjusted to bias the sum in favour of some part of the "window".

It can occur that contractions of the oesophagus may be stimulated, for example by movement of the patient during an operation. The inclusion of signals due to such stimulation may give rise to misleading estimations of degree of anaesthesia. For this reason, it is preferable to provide as a function of the apparatus manual selective rejection means 23A for selectively rejecting any particular signal at the discretion of the operator, such that the particular signal does not contribute to the degree of anaesthesia indicated.

The output from circuit 24 is applied to an inverter 25 to give a rate of contraction and this rate is displayed in an analogue display 26, for example as a bar of varying length. Alternatively or in addition it is displayed in digital form in a digital display 27.

It may be desired to have a visual record of oesophageal activity. A temporary record may be shown on a cathode ray tube or similar display. A permanent record may be obtained with a chart recorder 28 which is fed with the signal from transducer 21. Recorder 28 can also carry indications of the input pulses to timer/counter circuit 24 by feeding signals from circuit 23 to an event marker 29 to provide a suitable indication on the chart of the occurrence of each supra-threshold signal. Additionally the operation of valve 8 may be recorded by a second event marker 34 triggered from a line 35 from timing unit 12. Thus, as well as providing a record of oesophageal activity, the chart recorder may also produce a separate record of those sensed pulses greater than the preset threshold value, and the inflation of the provoking balloon.

A typical trace obtained from apparatus as illustrated in FIG. 1 is shown in FIG. 6, in which the lower trace 41 represents the amplitude of provoking pulses applied to balloon 5, and the upper trace 42, represents the amplitude of pressure-waveform sensed by the liquid-filled balloon 4. Upper trace 42 can be seen to consist of a regular background pattern of pressure-waves 43 approximately 10 mm Hg. in amplitude due to forced ventilation of the lungs of the patient. On the top of this regular trace 43 are superimposed waveforms 45 of much greater amplitude, typically 30 to 50 mm Hg., each following a provoking pulse 44 by a matter of some 5 to 10 seconds. The occurrence or non-occurrence of these provoked pressure waves 45, above a preset threshold magnitude, for example 25 mm Hg. can be used as a simple "on-off" indication of whether the depth of anaesthesia of the patient is greater or less than a desired level.

The equipment thus far described operates to monitor depth of anaesthesia. However the signal from inverter 25 can be used directly to control the delivery of anaesthetic drugs to a patient. Drugs may be delivered to a patient by two routes depending on the type of drug used. Certain drugs may be given as a solution administered by controlled intravenous infusion for example by means of a syringe pump or drip controller. Where the anaesthetic drug is a gas or volatile liquid it may be administered by inhalation of a gas or vapour mixture produced by controllable gas mixing valves and vapourising systems. Where drug delivery is by means of a syringe pump loaded with the appropriate drug, the plunger of the syringe may be driven by a stepper motor. The rate of drive pulses supplied to the stepper motor determines the rate of delivery of the drug. Comparison of the rate signal from inverter 25 with a value set by the anaesthetist enables a control signal to be obtained which either speeds up or slows down the drive pulse rate of a syringe pump stepper motor in accordance with whether the rate signal that is monitored is above or below the set value.

The equipment required for this control function comprises a comparator 31 which is fed with the output from inverter 25. Comparator 31 also has fed to it a desired rate which is set by the anaesthetist. Comparator 31 compares the actual rate of contraction of the oesophagus with the desired rate and provides an error signal giving the magnitude and sign of the difference between the actual rate and the desired rate set by the anaesthetist. The error signal is applied to a pulse generator 32 to modify the rate of pulse generation therefrom. The pulse output from generator 32 is in the form of drive pulses to a stepper motor 33 which drives a syringe pump.

An alarm 30 is preferably included to give an audible or visual alarm or both. Triggering of a alarm 30 may be caused when the signal from inverter 25 falls below or rises above set safety levels. Additional alarm trigger signals can be obtained from various parts of the circuit, for example from pulse generator 32 if the pulses similarly are above or below set safety levels.

Many of the functions of the monitoring and control equipment of FIG. 2 can be incorporated in an appropriately programmed microprocessor. The inputs to the microprocessor include the signal from filter 22 as well as the various set values such as pressure threshold, window length and the desired rate of contractions. The output from the microprocessor includes display information and signals to control pulse generator 32. Conditions for operating alarm 30 can also be incorporated.

The pattern of oesophageal contractions, e.g. the amplitude, rate, degree of repetition of any particular sequence of contractions, may be characteristic for a particular patient. This allows the possibility of providing for the apparatus to be adaptive, in the sense that the microprocessor can be programmed to generate a response "norm" for a particular patient, based on observation over a period, and to produce an output corresponding to deviation from the norm, whether in amplitude, rate, or any other parameter of the contractions, which will indicate the degree of anaesthesia.

Before being processed, signals from the transducer may be converted from analogue to digital form, and the digitised form of the input may be connected directly to the microprocessor circuitry. Using this technique it is possible for the microprocessor to compare the output signal directly with a pre-programmed "norm", as regards for example amplitude, duration, and profile or "shape". If the signal fits the pre-set norm the waveform is recognised as a significant contraction. Clearly it may be useful to employ a threshold discriminator in combination with the above technique.

The amplitude of the contractions of the oesophagus has been found to vary along the length of the oesophagus, and to be greatest approximately 5 to 10 cm from the entry to the stomach. It is therefore preferable to provide means for retaining the sensor in the appropriate position in the oesophagus, for example a balloon adapted to pass into the stomach where it is inflated to locate the sensor in the desired position.

FIGS. 3a to 5b show alternative embodiments of the oesophageal probe, the same reference numerals being used as in FIG. 1 to denote corresponding parts.

Figure 3A:
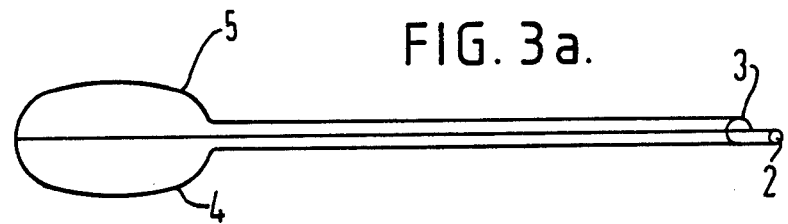
FIGS. 3 to 5b illustrate alternative constructions of oesophageal probes which may be used with the apparatus of FIG. 2.
Figure 3B:
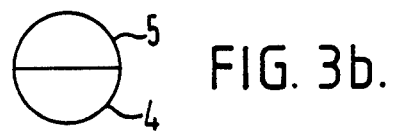

FIGS. 3a and 3b show respectively a schematic side and end view of an oesophageal probe, in which a provoking balloon 5 and a measuring balloon 4 are arranged in a parallel, rather than a series configuration. In use, the lumens 2 and 3 are connected as in FIG. 1.

Figure 4:
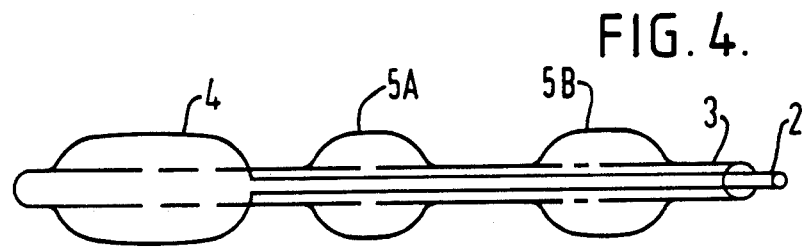

In the arrangement shown in FIG. 4, two provoking balloons, 5A and 5B are used. Thus, the oesophagus may be provoked in two positions simultaneously. By providing communicating holes of different sizes from the balloons shown in 5a and 5b to the outer lumen 3, the rate of expansion of the balloons 5A and 5B may be made to differ from each other, so as to give a peristaltic-like effect. Multiple balloons of this kind may be utilised with any of the probe designs proposed herein.

Figure 5A:
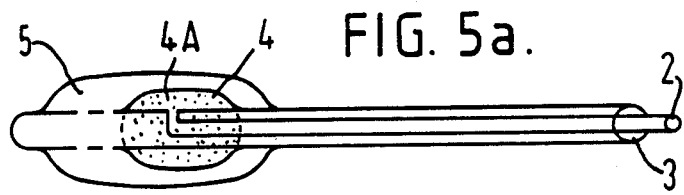
Figure 5B:
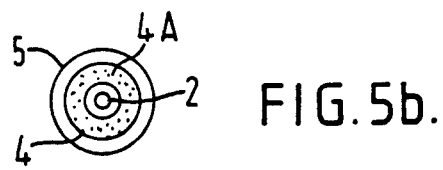

FIGS. 5a and 5b show side and end schematic views respectively of a probe in which a provoking balloon 5 is provided concentric with a sensing balloon 4. The sensing balloon continues to be sensitive to pressure changes, provided that the provoking balloon is deflated. During the application of brief provoking pressure pulses to the provoking balloon 5, the sensing balloon 4 is not responsive to changes in oesophageal activity, but sensitivity returns to normal, when the provoking pulse has ceased.

A number of other modifications may be used with the probes described above. For example, the sensing balloon may be provided with a foam insert 4A, to maintain the balloon volume. This is particularly useful when the sensing balloon is gas filled, since a contraction of the oesophagus will give rise to a greater pressure signal.

When the sensing balloon is gas filled, progressive drift in the system pressure is likely to occur, due to both temperature change of gas within the balloon, and by the diffusion of anaesthetic gases, for example, nitrous oxide, from the body tissues through the balloon wall. It is therefore desirable when a gas filled sensing balloon is used to incorporate a small controlled leak into the gas line connected to the monitor balloon, to allow very slow equalisation of any progressive pressure drift. The leak is not, of course, so large as to interfere significantly with the transmission of transient high pressure signals. Instead of a fluid-filled balloon for pressure sensing, a pressure transducer may be inserted into a soft sleeve in place of balloon 4. This may be combined with means for provoking the oesophagus to contraction, for example, a pressure balloon of the kind described above.

As an alternative to a balloon for provoking the oesophagus to contraction, a pair of spaced stimulating electrodes may be provided, and these may be spaced along the length of a balloon type catheter used for sensing oesophageal pressure.

In yet a further alternative embodiment, provocation of the oesophagus may be carried out by a suitable balloon inserted into the trachea of the patient.

Any of the oesophageal probes discussed above may have incorporated therein a microphone, a temperature probe, or electrodes for recording an electrocardiogram. The microphone may be either incorporated in the region of the probe tip, or else connected either to the provoking lumen 3, or sensing lumen 2, sound from the oesophagus being transmitted by the intermediate fluid. Thus, a stethoscope function may be provided.

Similarly, a temperature probe, for example a thermistor, may be provided in the probe tip to record body temperature.

A particularly preferred embodiment of an oesophageal probe for use in the method of the invention is illustrated in FIG. 8. The probe of FIG. 8 includes two sensing balloons, 84a and 84b each connected to separate transducers via passageways 82a and 82b respectively. The two sensing balloons each have a length of approximately 3 to 5 cm, and a maximum diameter of approximately 2 cm.

Approximately 1 cm from the distal sensing balloon, 84a, is a single provoking balloon 85. The provoking balloon 85 is in communication via holes 86 with a passageway 83, through which provoking pulses can be applied, in the same way as described above. The distance between the provoking balloon 85 and the monitoring balloon 84b is approximately 5 cm.

The provision of two transducers linked to passageways 82a and 82b enables oesophageal pressure to be monitored at two points in the oesphagus spaced by approximately 10–15 cm.

The human oesophagus is unusual in that it has a nervous control mechanism which controls the whole of the oesophagus, despite the fact that the lower part is made of involuntary or "smooth" muscle, and the upper part of voluntary or "skeletal" muscle. The ability to measure oesophageal contractions at two points spaced in the oesophagus, using a probe as illustrated in FIG. 8, is a useful one, since there are certain drugs, for example curare-like muscle relaxants, which selectively paralyse "skeletal", but not "smooth" muscle.

When muscle relaxants have been given to a patient, oesophageal contractions can only be elicited in the lower part of the oesophagus. As the muscle relaxant wears off (the half-life of many relaxants is around 15 to 20 minutes) an increasing amount of activity can be recorded in the upper oesophagus. Thus, the relative amplitude of contractions in the upper and lower oesophagus provides a means for assessing the extent of skeletal muscle paralysis.

FIG. 9 is a block schematic diagram illustrating a circuit suitable for use with the probe of FIG. 8 to make use of this effect.

Balloons 84a and 84b are connected to transducer a and transducer b respectively, and the amplitude of the signals is compared in a comparator. The comparator may function continuously, activated by contractions in excess of a threshold value, or by any of the other identification method outlined above, as monitored by the distal monitoring balloon 84a. Alternatively, the system may operate only when enabled by a signal from the provoking unit.

When the provoking balloon 85 is inflated, provoked contractions will be observed in both sensing balloons 84a and 84b within 5 to 10 seconds. Thus, the arrangement will normally provide for the comparator to be enabled for a period of from 5 to 10 seconds. The display provides an output corresponding to the ratio of amplitudes of pressure sensed by balloons 84b and 84a. When this ratio is near unity, there is little muscle paralysis. When the ratio is close to zero, skeletal muscle is paralysed fully.

Thus, according to yet a further embodiment of the invention, there is provided a method for determining the degree of skeletal muscle relaxation of a patient, which method comprises providing signals indicative of contractions at two spaced points in the oesophagus of a patient, and comparing the signals to derive therefrom an output indicative of the degree of skeletal muscle relaxation of the patient. The invention includes within its scope apparatus for carrying out the above method.

A number of the probes described above are in themselves novel, and such probes should be considered as lying within the scope of this aspect of the invention.

A preferred embodiment of the second aspect of the invention discussed above, involving allocating a "score" for various bodily functions is illustrated in more detail with reference to FIG. 7, and the following table. The table illustrates a suitable scoring system for the four parameters systolic blood pressure, heart rate, sweat, and tears.

TABLE

| INDEX | CONDITION | SCORE |
| --- | --- | --- |
| SYSTOLIC BLOOD PRESSURE (mm Hg) | LESS THAN CONTROL + 15 | 0 |
| | LESS THAN CONTROL + 30 | 1 |
| | MORE THAN CONTROL + 30 | 2 |
| HEART RATE (beats/min) | LESS THAN CONTROL + 15 | 0 |
| | LESS THAN CONTROL + 30 | 1 |
| | MORE THAN CONTROL + 30 | 2 |
| SWEAT | NIL | 0 |
| | SKIN MOIST TO TOUCH | 1 |
| | VISIBLE BEADS OF SWEAT | 2 |
| TEARS OR LACRIMATION | NO EXCESS TEARS WITH EYELIDS OPEN | 0 |
| | EXCESS TEARS VISIBLE | 1 |

TABLE-continued

| INDEX | CONDITION | SCORE |
| --- | --- | --- |
| | WITH EYELIDS OPEN TEAR OVERFLOW FROM CLOSED EYELIDS | 2 |

In the illustrated embodiment each of these functions is assigned one of three score values 0, 1 or 2. Clearly, a different number of values and a different value system can be used if desired. The total score of the four functions in the above system can thus vary from 0 to 8. A low score would be characteristic of deep anaesthesia and a high score of light anaesthesia. The four functions that are selected are systolic blood pressure, heart beat rate, sweating and tears. The first two are obtained by direct measurements of the patient while the last two functions are assessed by a clinician. In the embodiment illustrated the measured or assessed values are entered by the clinician via a keypad, although in an alternative embodiment, suitable electrical transducers may be used to measure one or more of the functions directly, the transducers providing the appropriate electrical input to the apparatus.

In the case of blood pressure and heart beat it is the deviation from control values that is used in determining a score value and these control values are obtained from the patient by measurement beforehand. The scoring system shown in the table of FIG. 6 may be modified to include additional or alternative functions. Clearly a different set of score values can be used giving a smaller or greater number of ranges.

Suitable equipment incorporating the scoring system shown in the table is shown in FIG. 7. The equipment provides for the input of parameters of four bodily functions. These are systolic blood pressure (indicated by BP), heart beat rate (indicated by HR), sweating (indicated by SW) and tears or lacrimination (indicated by TE). Initially suitable thumbwheel switches 51 are set to give control values of BP and HR. These values are fed to a comparator 52 to which the current measured values of BP and HR are also fed. These values may be measured by suitable transducers. Comparator 52 carries out the appropriate calculation for determining in which of the three ranges of measurement set out in FIG. 6 the measured values lie and provides outputs of numerical values 0, 1 or 2 as appropriate. These values are fed to a summing circuit 53. There are also further inputs to summing circuit 53. These are the score values of the functions SW and TE as assessed by the clinician. Summing circuit 53 adds all the score values and displays the total score in a display unit 54 which may be analogue or digital, or both if desired.

An alarm circuit 55 may be provided to give an audible or visual alarm or a combination thereof if the total score is above or below preset limits. The maximum and minimum score limits may be entered by thumbwheel switches 56 and the output of circuit 53 may be compared in a comparator 57 with the score limits set by switches 56 to determine whether alarm 55 needs to be activated.

To enable the required rate of administration of a drug to be displayed a further comparator 58 is provided which has as one input a desired score level set by a thumbwheel switch 59 and as its other input the total score output from circuit 53. The output of comparator 58 is an error function which is a measure of the difference between the desired or required level of anaesthesia and the level which is obtained from measurement and assessment. This error function is fed to a drug rate calculator 60 which has as a preset input an initial drug rate obtained from a thumbwheel switch 61 which is set by the clinician. Calculator 60 modifies the value of the initial drug rate held in switch 61 in accordance with the error function obtained from comparator 58 and displays the required drug rate in a display 62. This calculation may be carried out at intervals as controlled by a clock 63.

The equipment thus far described enables the depth of anaesthesia of a patient to be monitored and additionally displays information as to the required rate of administration of drugs to achieve a desired depth of anaesthesia. Since the equipment provides such information it can also include means for automatically delivering drugs at the required rate.

Drugs may be delivered to patients by two routes depending on the type of drug used. Some drugs are given as a solution administered by controlled intravenous infusion from for example a syringe pump or drip controller. Where the anaesthetic drug is a gas or volatile liquid it may be administered by inhalation of a gas or vapour mixture produced by controllable gas mixing valves and vaporising systems. Where drug delivery is by means of a syringe pump loaded with the appropriate drug, the plunger of the syringe may be driven by a stepper motor. The rate of drive pulse supplied to the stepper motor determines the rate of delivery of the drug. Comparison of the current total score with the desired score set by the anaesthetist enables a control signal to be obtained which either speeds up or slows down the drive pulse rate to the syringe pump stepper motor in accordance with whether the score value that is monitored is above or below the set value.

An example of additional items of equipment to control the administration of drugs is also shown in FIG. 7. The output from calculator 60 giving the required drug rate is switched through a switch 64 if automatic control is desired to a comparator 65. Comparator 65 has inputs from thumbwheel switches 66 which give the maximum and minimum limits of drug rates. If the input from drug rate calculator 60 is outside the limits set by switches 66 then an alarm 67 is energised. If the output from calculator 60 is within the set limits then this value is fed to a variable frequency oscillator 68 to control the frequency thereof in accordance with the value of the output of calculator 60. Oscillator 68 controls the speed of operation of a stepper motor 69 which operates a suitable syringe pump or the like for drug infusion. A drug rate setting circuit 70 may be interposed in the input path to oscillator 68 to enable the rate of drug supply to be changed manually. The total amount of drug supplied is displayed in a display 71 fed from oscillator 68.

Whilst the above description relates primarily to patients undergoing anaesthesia for surgery, the apparatus described herein can readily be used for patients to whom sedative, muscle relaxant and/or analgesic drugs may be administered, for example in intensive care units, and the terms "anaesthetic" and "anaesthesia" in the following claims should be understood accordingly.

We claim:

1. Patient monitoring apparatus, comprising a sensor for providing signals indicative of smooth muscle contractions in the oesophagus of a patient, means for deriving from the said signals an output indicative of the depth of anaesthesia of a patient, and means adapted to connect said output deriving means to a device which operates in response to said derived output.

2. Apparatus as claimed in claim 1, including discriminating means for accepting only signals of more than a desired threshold magnitude to eliminate signals arising out of non-oesophageal activities.

3. Apparatus as claimed in claim 2, wherein the said threshold magnitude is greater than the magnitude of signals produced by forced ventilation of the lungs of the patient.

4. Apparatus as claimed in claim 2, further including means for defining a preset time window during which oesophageal contractions are measured, and means for continuously measuring the number of oesophageal contractions greater than said desired threshold magnitude which occur within said preset time window.

5. Apparatus as claimed in claim 1, including means for stimulating contractions in the oesophagus of the patient.

6. Apparatus as claimed in claim 5, wherein the means for stimulating contractions in the oesophagus comprise a balloon insertable into the oesophagus or the trachea and means for applying pressure to the balloon.

7. Apparatus as claimed in claim 4, including means for supressing stimulation of the oesophagus on detection of spontaneous oesophageal contractions by the sensor.

8. Apparatus as claimed in claim 1 wherein said means deriving an output indicative of the anaethesia depth includes means for producing an output indicative of the rate of occurrence of oesophageal contractions.

9. Apparatus as claimed in claim 1, which apparatus includes means for selectively rejecting any signal at the discretion of the operator of the apparatus.

10. Apparatus as claimed in claim 1, wherein the sensor includes a balloon insertable into the oesophagus of the patient, and transducer means for producing an electrical signal in response to pressure changes in said space in the balloon.

11. Apparatus as claimed in claim 1 further including means for automatically rejecting signals of less than a predetermined duration.

12. Patient monitoring apparatus as in claim 1, which further comprises means for assigning a score value to each of a plurality of different bodily functions of a patient, the said score values being indicative of a depth of anaesthesia or sedation and one of the said score values being indicative of contractions in the oesophagus, means for summing the score values, and means for producing an output from the summed score values indicative of the amount of anaesthetic to be fed to the patient.

13. Apparatus as claimed in claim 12, including means for prompting the entry by a clinician of a score value.

14. Apparatus as claimed in claim 12, wherein the bodily functions include heart rate, blood pressure, degree of sweating, and formation of tears.

15. Apparatus for controlling the amount of an anaesthetic administered to a patient comprising sensor means for providing signals indicative of contractions in the oesophagus of a patient, means for deriving from said signals an output indicative of the depth of anaesthesia of a patient, and means for automatically controlling the amount of an anaesthetic administered to a patient in response to variation in the output indicative of the depth of anaesthesia.

16. Apparatus for monitoring the depth of anaesthesia of a patient, which apparatus comprises means for stimulating contractions in the oesophagus of the patient, a sensor for providing signals indicative of the oesophageal contractions, discriminating means for accepting only signals of more than a preset threshold magnitude to eliminate signals arising from non-aesophageal activities, and means for deriving from the signals an output indicative of the rate of occurrence of signals having a magnitude greater than said preset threshold magnitude.

17. A method of monitoring the depth of anaesthesia in a patient, which method comprises the steps of (a) deriving signals indicative of contraction in the oesophagus of the patient, and (b) deriving from the said signals an output indicative of the depth of anaesthesia of the patient.

18. A method as claimed in claim 17, wherein step (b) further includes the step of deriving the output only from signals having a magnitude greater than a desired threshold value.

19. A method as claimed in claim 17, wherein step (b) further includes the step of deriving the output from the rate of occurrence of the said oesophageal contractions.

20. A method as claimed in claim 17 further comprising the step of (c) applying a stimulus to the patient to provoke contractions in the oesophagus.

21. A method of controlling the depth of anaesthesia of a patient, which method comprises the steps of (a) deriving signals indicative of contractions in the oesophagus of the patient, (b) deriving from the signals an output indicative of the depth of anaesthesia of the patient, and (c) controlling the administration of anaesthetic or sedative drugs to the patient in response to the said output.

22. A method as claimed 21, wherein step (b) further includes the step of deriving the output only from signals having a magnitude greater than a desired threshold value.

23. A method as claimed in claim 21, wherein step (b) further includes the step of deriving the output.

24. A method as claimed in claim 21 further comprising the step of (d) applying a stimulus to the patient to provoke contractions in the oesophagus.

25. An elongate probe for measuring oesophogeal contractions, having a distal end adapted to pass downwardly through the oesophagus of the patient, and a proximal end adapted in use to lie externally of the mouth of the patient, the probe including stimulating means adapted in use to lie within the oesophagus of a patient and operable by means external to the patient for stimulating the oesophagus, to cause contractions therein, pressure sensing means adapted in use to lie within the oesophagus of the patient for enabling the measurement of pressure within the oesophagus, thereby to sense contractions of the oesophagus.

26. A probe as claimed in claim 25 wherein the stimulating means comprises a sealed inflatable balloon, and the probe comprises a lumen in fluid communication between the balloon and the proximal end of the probe.

27. A probe as claimed in claim 26 wherein the maximum diameter of the inflatable balloon is about 2 cm.

28. A probe as claimed in claim 27 wherein the stimulating means comprises two inflatable balloons spaced along the probe.

29. A probe as claimed in claim 28 including means to cause the two inflatable stimulating balloons to expand at differing rates.

30. A probe as claimed in claim 25 wherein the stimulating means includes a pair of electrodes on the probe, and means for supplying an electrical voltage to the electrodes.

31. A probe as claimed in claim 30 wherein the pressure sensing balloon includes a foam insert to maintain the balloon volume.

32. A probe as claimed in claim 25 wherein the pressure sensing means includes an inflatable sensing balloon.

33. A probe as claimed claim 32 including a lumen in fluid communication between the said sensing ballon and means on the proximal end of the tube for the connection of a pressure transducer.

34. A probe as claimed in claim 32 wherein the maximum diameter of the sensing balloon is about 2 cm.

35. A probe as claimed in claim 32 wherein the sensing balloon has a length of from 3 to 5 cm.

36. A probe as claimed in claim 32 wherein a small leak is provided to permit the equalisation of permanent pressure changes in the sensing balloon.

37. A probe as claimed in claim 32 which also incorporate a sealed inflatable stimulating balloon as defined in claim 26.

38. A probe as claimed in claim 37 wherein the stimulating balloon and the sensing balloon are concentric.

39. A probe as claimed in claim 25 including a pressure transducer adapted in use to lie in the oesophagus of the patient.

40. A probe as claimed in claim 25 including means for sensing the pressure at two points spaced along the oesophagus.

41. A probe as claimed in claim 4 wherein the said points are spaced from each other by from 10 to 15 cm.

42. A probe as claimed in claim 25 including a microphone or a temperature sensor.

43. A probe for measuring oesophogeal contractions, comprising an elongate body portion for insertion into the oesophagus and having at least first and second lumens sealed with respect to each other, the first lumen being in communication at its distal end with a sensing balloon for sensing oesophageal pressure, and being provided at its proximal end with means for connection to a pressure measuring device, and the second lumen being adapted to receive a fluid under pressure to stimulate the oesophagus to cause contractions therein.

44. Patient monitoring apparatus, which comprises means for assigning a score value to each of a plurality of different bodily functions of a patient, the said score values being indicative of a depth of anaesthesia or sedation, means for summing the score values, and means for producing an output from the summed score values indicative of the amount of anaesthetic to be fed to the patient.

45. Apparatus as claimed in claim 14, including means for measuring at least one of the said bodily functions.

46. Apparatus as claimed in claim 44, including means for prompting the entry by a clinician of a score value.

47. Apparatus as claimed in claim 44, including means for automatically controlling the amount of anaesthetic delivered to the patient in response to the said output.

48. Apparatus as claimed in claim 47, wherein the bodily functions include heart rate, blood pressure, degree of sweating, and formation of tears.

49. A method of monitoring the depth of anaesthesia of a patient, which method comprises assigning a score value to each of a plurality of different bodily functions, the said score values being indicative of a depth of anaesthesia, and summing the score values to obtain a total score indicative of the depth of anaesthesia of the patient.

* * * * *